United States Patent [19]

Redmond et al.

[11] Patent Number: 4,500,311
[45] Date of Patent: Feb. 19, 1985

[54] EXTERNAL VENTRICULAR DRAINAGE ASSEMBLY

[75] Inventors: Russell J. Redmond; Jessica B. Ash, both of Santa Barbara, Calif.

[73] Assignee: American Hospital Supply Corporation, Evanston, Ill.

[21] Appl. No.: 469,060

[22] Filed: Feb. 23, 1983

[51] Int. Cl.³ .............................................. A61M 5/00
[52] U.S. Cl. .................................... 604/246; 604/323; 604/325; 128/768
[58] Field of Search ...................... 604/246, 30, 8–10, 604/32, 118, 128, 174, 326, 247, 248, 251, 255, 322–326, 283; 128/768

[56] References Cited

U.S. PATENT DOCUMENTS

| | | | |
|---|---|---|---|
| 3,157,201 | 11/1964 | Littmann | 604/32 X |
| 3,604,420 | 9/1971 | Vaillancourt | 604/323 |
| 3,906,935 | 9/1975 | Raia | 604/325 |
| 3,957,050 | 5/1976 | Hines, Jr. | 604/118 |
| 4,103,689 | 8/1978 | Leighton | 604/9 |
| 4,175,552 | 11/1979 | Hess et al. | 604/246 |
| 4,402,682 | 9/1983 | Garver et al. | 604/283 X |
| 4,435,174 | 3/1984 | Redmond et al. | 604/174 |

*Primary Examiner*—Stephen C. Pellegrino
*Attorney, Agent, or Firm*—Roger A. Williams

[57] ABSTRACT

An external ventricular drainage assembly includes a ventricular drainage catheter which can be placed in the ventricles of a patient's brain and which is connected to a suture tab for securing the catheter to the patient and for preventing relative movement between the catheter and patient. A valve is connected to the catheter for selectively opening and closing the external ventricular drainage assembly to fluid flow. An adapter is connected to the valve for providing access to the fluid flow path within the assembly. A one-way valve is connected to the adapter. A first length of flexible tubing is connected to the one-way valve and is joined through a connector to a second length of flexible tubing. A collection reservoir is connected to the second length of flexible tubing and includes an entry and outlet port. A drip chamber is positioned between the second length of flexible tubing and the collection reservoir.

22 Claims, 1 Drawing Figure

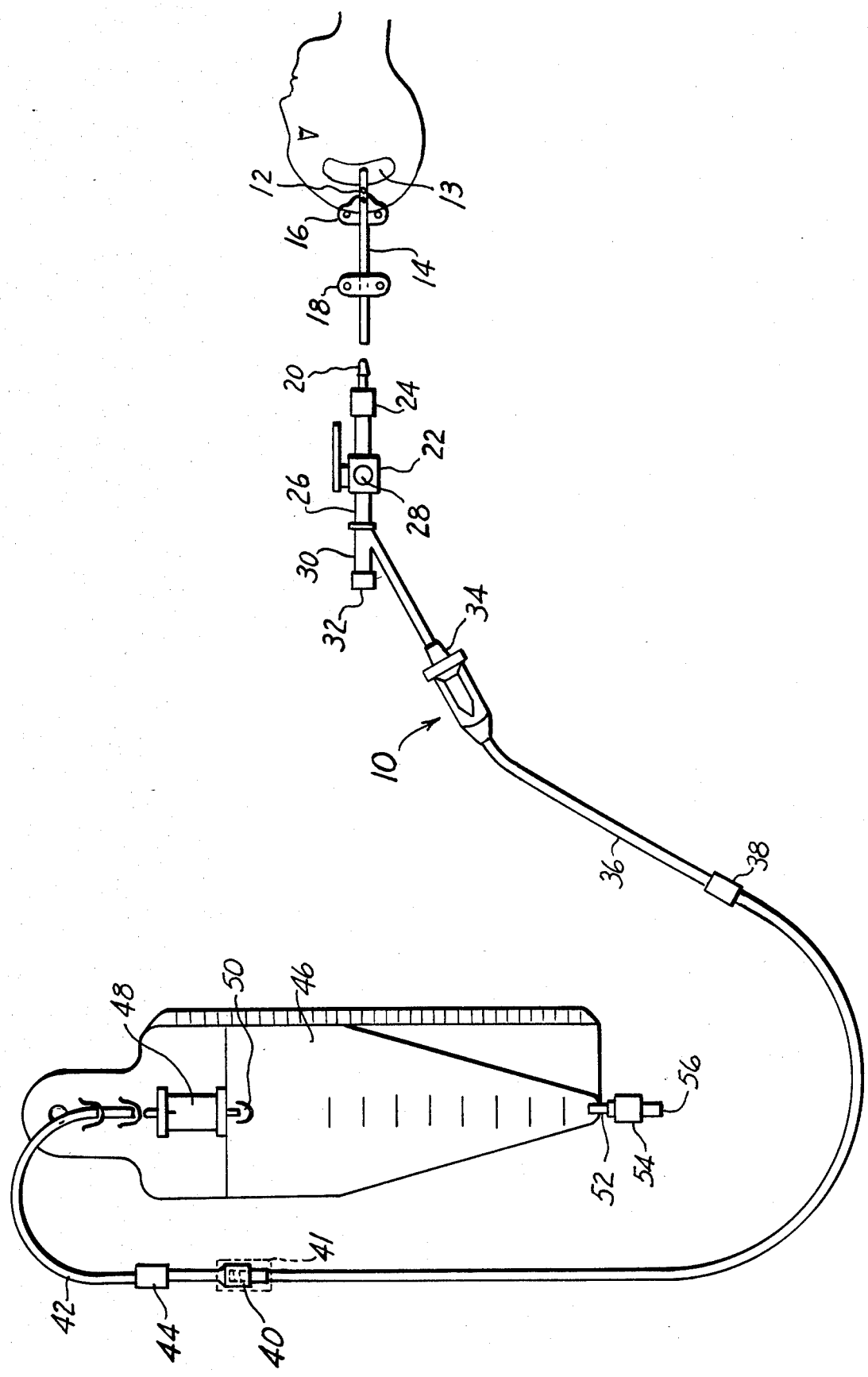

EXTERNAL VENTRICULAR DRAINAGE ASSEMBLY

BACKGROUND OF THE INVENTION

The invention herein relates to an external ventricular drainage assembly for use in the draining of cerebrospinal fluid (CSF) from the ventricles of a patient's brain to prevent the undue buildup of such CSF and pressure within the brain.

The external ventricular drainage assembly herein is designed for use in the treatment of hydrocephalus wherein excess cerebrospinal fluid is drained from the ventricles of the brain. In many known techniques for the treatment of hydrocephalus, excess CSF is drained from the ventricles of the brain to another region of the body such as the right atrium or the peritoneum. In such systems, a valving mechanism is employed which is implanted in the patient. The valving mechanism permits the flow of the excess CSF from the brain to such other parts of the body.

Under some circumstances, it is desirable to treat hydrocephalus by draining the excess CSF from the ventricles of the brain to a collection receptacle that is outside of the body. For example, surgically induced hydrocephalus may be only a temporary problem such that it would not need a totally implanted CSF shunting system. In such a case, an external drainage system is desirable.

Problems associated with external drainage systems which drain fluid from the body, regardless of the fluid, generally relate to such systems providing routes of infection to the patient. An external drainage system which is open to the environment surrounding a patient can provide a route for microbes such as bacteria to enter the patient's body. It is undesirable to have the possibility for the introduction of bacteria to cause an infection to the patient as generally the patient is already in a weakened condition. It would be desirable to provide an external ventricular drainage assembly which would prevent or inhibit the introduction of bacteria and other microbes into the patient and which would be an easy to use system.

SUMMARY OF THE INVENTION

The external ventricular drainage assembly herein provides an assembly for draining excess CSF from the ventricles of a patient's brain to an external collection reservoir.

The external ventricular drainage assembly herein includes a ventricular drainage catheter which can be implanted within the ventricles of a patient's brain and extends outside the patient's body. The catheter can be anchored to the patient through a suture tab to prevent relative movement of the catheter and patient. The catheter is connected to a valve which can open and close to permit or prevent fluid flow through the catheter and assembly. The valve can be a two or three ported stopcock.

Connected to the valve is a Y-tube which includes an injection site. Also connected to the Y-tube is a one-way valve which permits flow of fluid in one direction, outwardly of the patient, through the assembly. The one-way valve is connected to a suitable length of tubing which in turn is connected to a second length of tubing through a connector. The connector consists of two parts which interconnect, providing fluid flow between the lengths of tubing. A tamper-evident closure can extend around the connector to show when the connector has been disconnected.

Connected also to the second length tubing is a collection reservoir. The collection reservoir has an inlet which is connected to the second length of tubing through a drip chamber. The reservoir also includes an outlet for draining collected fluid. The outlet can include a withdrawal site whereby samples of collected fluid can be withdrawn from the reservoir, or whereby the collection reservoir can be emptied without opening the system.

The collection reservoir can be appropriately marked with graduations indicating the volume of fluid collected and the height position of the collection reservoir relative to the patient.

BRIEF DESCRIPTION OF THE DRAWING

The enclosed drawing is an elevational view of an embodiment of an external ventricular drainage assembly.

DETAILED DESCRIPTION OF THE INVENTION

With reference to the drawings, there is shown a working embodiment of an external ventricular drainage assembly which can be used to drain or transfer CSF from a patient to an external collection reservoir remote from the patient. The assembly can be used for either short term or long term transfer of CSF from the ventricles of a patient's brain to a collection reservoir for lowering the fluid pressure within the ventricles of the brain of the patient.

With reference to the drawing, the external ventricular drainage assembly 10 is shown. The assembly includes a drainage catheter 14 which can be a ventricular drain 12. The drainage catheter can be any suitable drainage catheter and generally has the structure of a catheter having apertures along a portion of its length for receiving CSF. The drainage catheter extends from the ventricles 13 outwardly of the skull of the patient through a suitable burr hole and along and under the scalp to an exit site. The catheter then extends outwardly from the patient. The catheter can be held in place to prevent relative movement of the catheter and patient by a suture tab 18. The suture tab can be sutured to the patient to prevent relative movement of the catheter.

In some applications it is desirable to employ a catheter guide 16 for holding the catheter in position within the patient's brain. The catheter guide can also be fixed to the patient such as by suturing to the scalp.

The catheter is connected to a valve 22. The catheter can be connected directly to the valve or can be connected through a catheter connector 20. The catheter connector 20 can be a connector which provides either a slip fit, twist lock, or screw-type connection to a port on the valve.

The valve 22 can be any suitable valve which permits the opening and closing of the assembly to fluid flow. That is, the valve can be selectively positioned to permit CSF flow through the assembly or to prevent CSF flow through the assembly. Suitable valves can be a two port or three port stopcock as is shown in the drawing. In the drawing, the valve 22 is a three port stopcock with an inlet port 24 to which the catheter is connected, an outlet port 26, and a third port which can be a pressure monitoring port 28. Such a third port is desirable as it can permit the monitoring of fluid pressure within the assembly which in turn can be correlated to the fluid pressure within the patient's brain. A pressure transducer can be interconnected to such a pressure monitoring port 28 on the valve.

Connected to the outlet port of the valve is an adapter for monitoring intracranial pressure such as Y-tube 30. The adapter includes an injection site 32. The injection site can be a self-sealing material which permits the insertion of a needle cannula for withdrawing a sample of the fluid within the assembly or injecting fluids into the brain. In some embodiments of the assembly, the injection site need not be on such an adapter. That is, a third port on a stopcock valve can be utilized as a sample port or can be equipped with an injection site for injecting fluids or withdrawing samples of the CSF. In such an embodiment, the outlet port of the valve can be directly connected to the next element which is a one-way valve 34.

Also connected to the adapter 30 is a one-way valve 34. The one-way valve can be any suitable valve for permitting fluid flow through the assembly in one direction; i.e., outwardly of the patient. Suitable one-way valves include a miter valve as is shown in the drawing.

Connected to the one-way valve is a first length of tubing 36. The first length of tubing can be of any sufficient length depending on the election of the end user and the desired placement of the drainage reservoir from the patient. Such a first length of tubing can be provided with a clamp 38 which can, when its in its clamped position, close the tubing to fluid flow therethrough. Closing the clamp is a backup to the one-way valve to also insure fluids injected through injection site 32 are delivered to the brain.

The first length of tubing is connected to a second length of tubing 42 through a coupling 40. The coupling 40 can include two separate interconnecting elements each of which is respectively connected to the first and second lengths of tubing. The elements of the coupling interlock to provide a fluid-tight coupling between the first and second lengths of tubing. Extending around the coupling 40 can be a tamper-evident seal 41. The tamper-evident seal can be a stretch-fitted plastic band or other suitable material which can be adhered to the two elements of the coupling, such that when the elements of the coupling are disconnected, the disconnection shows by the rupturing or tearing of the tamper-evident seal. By providing a tamper-evident seal to the coupling, any opening of the coupling can be readily observed by the user. A clamp can be positioned along the second length of tubing for occluding the second length of tubing to fluid flow therethrough.

The second length of tubing extends to and is connected to the collection reservoir 46. The collection reservoir 46 has an inlet port 50 which can be connected to the second length of tubing through a drip chamber 48. The drip chamber 48 can be useful in monitoring the flow rate of fluid through the assembly and can assist in the prevention or inhibition of bacteria migration through the assembly and to the brain. The reservoir can also be provided with an outlet port 52. The outlet port 52 can be equipped with a clamp for opening or closing the port to fluid flow. In the preferred embodiment of the assembly, the outlet port is provided with a withdrawal site 56. The withdrawal site can be a self-sealing material which permits the introduction of a needle cannula into the reservoir for obtaining a sample of the fluid therein or for emptying the collection reservoir. The withdrawal site reseals upon withdrawal of the needle cannula.

The outlet port can include a length of tubing extending between the reservoir and withdrawal site which can be cut to remove the withdrawal site and thereafter be closed with a clamp 54.

The preferred structure of the collection reservoir is as shown in the drawing. That is, the collection reservoir has a generally conical shape which permits ease of determining the volume of CSF collected. That is, for minor amounts of CSF collected the volume can be readily determined. The reservoir can be marked with graduations for determining the volume as is indicated in the drawing.

The collection reservoir can include along its side graduation markings as are shown in the drawing. Such additional markings are useful in positioning the reservoir and in determining the height of the collection reservoir relative to the patient. By placing the desired height of the height scale at the same level as the catheter inside the patient, the fluid pressure within the ventricles will be maintained and will prevent any siphoning action.

The external ventricular drainage assembly is useful in draining excess CSF from a patient. In operation, the ventricular drainage catheter is placed in the ventricles of the patient's brain, extended through a burr hole in the patient's skull and under a portion of the scalp of the patient, and exited through an opening in the scalp spaced from the burr hole. The catheter can be sutured to the patient's scalp to prevent relative movement.

Excess CSF in the ventricles drains into the ventricular drainage catheter and through the valve 22.

The valve 22 can be selectively positioned to permit the fluid to flow therethrough. In addition, the valve can be selectively positioned to permit monitoring through its pressure monitoring port of the fluid pressure within the assembly.

The CSF flows through the valve and into and through the one-way valve 34. If it is desirable to inject fluid into the brain or to obtain a sample of the CSF from the assembly, this can be done through the injection site 32. That is, the cannula of a syringe can be inserted through the injection site to obtain a sample of the fluid or deliver fluid to the system.

The CSF continues to flow through the one-way valve along the first and second lengths of tubing and drips through the drip chamber 48 and into the collection reservoir 46. The volume of CSF collected in the collection reservoir can be monitored by a doctor, nurse or attendant for the patient. It is possible to sample the CSF collected in the collection reservoir through the withdrawal site 56 by inserting a needle cannula of a syringe into and through the withdrawal site. It is also possible to obtain a sample by removing the withdrawal site and permitting the collected CSF to flow through the outlet port of the collection reservoir into a suitable receptacle. The collection reservoir can also be emptied through the withdrawal site by using a suitable needle cannula which can pierce the withdrawal site.

In some instances, the collection reservoir may become full and it would be desirable to exchange the reservoir with another. The collection reservoir can be removed from the assembly by disconnecting at the connector 40. A second collection reservoir with its drip chamber and second length of tubing can be connected to the remaining part of the connector 40 on the first length of tubing, thereby again permitting fluid flow through the entire assembly into such a second collection reservoir.

It is desirable to have a tamper-evident seal extending around the connector as the assembly herein described is essentially a closed system. Such a closed system is desirable as it prevents or inhibits the introduction of bacteria and other microbes to the patient. Once the system has been opened, more caution may need to be exercised to avoid introducing infection to the patient. Once the tamper-evident seal has been broken, the broken seal will alert the attendant to the fact that caution should be exercised to inhibit or prevent infection.

The fluid flows through the connector, through the second length of tubing and into the collection reservoir. The collection reservoir can be provided with a drip chamber through which the fluid flows. By monitoring the drip rate through the drip chamber, the rate of the fluid flow can be determined. The fluid is collected in the reservoir and its volume can be measured by appropriate graduations on the reservoir.

The collection reservoir can also be provided with a height scale along its side as indicated in the drawing. Such a height scale can provide for balancing the pressures. That is, balancing the level of liquid in the reservoir with the patient, to maintain the fluid pressure within the ventricles and avoid siphoning of the fluid.

If a sample of the fluid from the collection reservoir is desired, such a sample can be obtained through the withdrawal site on the outlet port. A needle cannula of a syringe can be inserted through the withdrawal site and a sample of the fluid obtained. Upon withdrawal of the needle, the withdrawal site seals upon itself, preventing any further flow of fluid.

If the collection reservoir becomes full and it is necessary to maintain the assembly attached to the patient for further drainage of CSF, then the fluid in the collection reservoir can be drained through the outlet port. This can be accomplished by cutting off the withdrawal site and allowing the fluid to drain. A clamp can then be inserted on the outlet port to prevent any further flow of fluid from the reservoir. The collection reservoir can also be drained by inserting a needle cannula of a syringe through the withdrawal site and withdrawing fluid until the bag is empty. This maintains a closed system. After draining the collected CSF, additional fluid can be collected in the same reservoir. This assembly also provides that should it be desirable to change collection reservoirs rather than drain the collection reservoir, the exchange can be accomplished readily by disconnecting the connector 40 between the first and second lengths of tubing. A second collection reservoir can then be reconnected to the connector 40.

The external ventricular drainage assembly herein can be provided in a kit form. Such a kit can contain each of the elements of the assembly shown in the drawing. By providing the assembly in a kit, the entire assembly can be sterilized and packaged or packaged and sterilized prior to its use. The kit also provides that the assembly can be preassembled with each of the components already connected to the other components which constitute the assembly. The kit in such a preassembled form provides a quick and easy drainage assembly which can be connected to the patient and once connected, is ready for use.

We claim:

1. An external ventricular drainage assembly comprising:

(a) a ventricular drainage catheter for placement in the ventricles of a patient's brain for receiving cerebrospinal fluid;
(b) retention means connected to the catheter for securing the catheter to the patient and for preventing relative movement between the catheter and patient;
(c) valve means connected to the catheter for selectively opening and closing the external ventricular drainage assembly to fluid flow;
(d) an adapter means connected to the valve means for providing access to the fluid flow path of the assembly;
(e) a one-way valve connected to the adapter means;
(f) a first length of flexible tubing connected to the one-way valve;
(g) coupling means having a first member connected to the first length of flexible tubing and a second member connected to a second length of flexible tubing, which first and second members interconnect to connect the first and second lengths of flexible tubing; and
(h) a collection reservoir for collecting cerebrospinal fluid, having an entry port which is connected to the second length of flexible tubing through a drip chamber and having an outlet port from which collected cerebrospinal fluid can be removed.

2. An external ventricular drainage assembly as recited in claim 1 wherein the valve means comprises a stopcock having two ports.

3. An external ventricular drainage assembly as recited in claim 1 wherein the valve means comprises a stopcock having three ports.

4. An external ventricular drainage assembly as recited in claim 3 wherein one of the ports on the three port stopcock is connected to a fluid pressure monitor.

5. An external ventricular drainage assembly as recited in claim 3 wherein one of the ports on the three port stopcock provides an injection site for obtaining samples of cerebrospinal fluid within the external ventricular drainage assembly.

6. An external ventricular drainage assembly as recited in claim 1 wherein the adapter means comprises a Y-tube connector including a self-sealing injection port.

7. An external ventricular drainage assembly as recited in claim 6 wherein the self-sealing injection port comprises a puncture resealable material.

8. An external ventricular drainage assembly as recited in claim 1 further comprising tamper-evident seal means extending around the coupling means for indicating when the first and second member of the coupling means have been disconnected.

9. An external ventricular drainage assembly as recited in claim 7 wherein the tamper-evident seal means comprises a rupturable band extending around the coupling means, which rupturable band ruptures upon disconnecting the first member from the second member of the coupling means.

10. An external ventricular drainage assembly as recited in claim 1 further comprising a closed self-sealing withdrawal site on the outlet port of the collection reservoir, which site can be penetrated by a cannula for obtaining a sample of collected fluid and which self seals upon withdrawal of the cannula.

11. An external ventricular drainage assembly as recited in claim 1 wherein the collection reservoir includes volumetric graduations for measuring the volume of fluid collected.

12. An external ventricular drainage assembly as recited in claim 1 wherein the collection reservoir comprises a flexible container which is generally conical in shape with the apex of the conical shape providing the bottom of the reservoir.

13. An external ventricular drainage assembly as recited in claim 1 further comprising a height scale on the collection reservoir.

14. An external ventricular drainage assembly as recited in claim 1 further comprising a catheter guide which can be secured to the patient and through which the catheter can be inserted for connection to the ventricular drain.

15. An external ventricular drainage assembly as recited in claim 1 wherein the retention means comprises a suture tab which can be sutured to the scalp of the patient.

16. An external ventricular drainage assembly as recited in claim 1 further comprising a clamp on the first length of flexible tubing for selectively opening or occluding the first length of flexible tubing to fluid flow therethrough.

17. An external ventricular drainage assembly as recited in claim 1 further comprising a clamp on the second length of flexible tubing for selectively opening or occluding the second length of flexible tubing to fluid flow therethrough.

18. An external ventricular drainage assembly as recited in claim 1 further comprising a clamp for selectively occluding or opening the outlet port on the collection reservoir to fluid flow therethrough.

19. An external ventricular drainage assembly comprising:
   (a) a ventricular drainage catheter for placement in the ventricles of a patient's brain for receiving cerebrospinal fluid;
   (b) retention means connected to the catheter for securing the catheter to the patient and preventing relative movement of the catheter and patient;
   (c) valve means including at least two ports for selectively opening and closing the external ventricular drainage assembly to fluid flow therethrough, one of the ports on the valve means connected to the catheter;
   (d) a one-way valve connected to a port on the valve means;
   (e) a first length of flexible tubing connected to the one-way valve;
   (f) coupling means having a first member connected to the first length of flexible tubing and a second member connected to a second length of flexible tubing for interconnecting the first and second lengths of flexible tubing; and
   (g) a collection reservoir for collecting cerebrospinal fluid, having an entry port and connected to the second length of fluid tubing through a drip chamber and having an outlet port from which cerebrospinal fluid can be removed.

20. An external ventricular drainage assembly comprising:
   (a) a ventricular drainage catheter for placement in the ventricles of a patient's brain for receiving cerebrospinal fluid;
   (b) a suture tab extending around the catheter for securing the catheter to the patient and preventing relative movement between the catheter and patient;
   (c) a three port stopcock connected to the catheter, which stopcock can be selectively opened and closed to fluid flow through the external ventricular drainage assembly;
   (d) a Y-tube connected to the three port stopcock and having a self-sealing injection port;
   (e) a one-way valve connected to the Y-tube;
   (f) a first length of flexible tubing connected to the one-way valve;
   (g) a coupling having a first member connected to the first length of flexible tubing and a second member connected to a second length of flexible tubing for interconnecting the first and second lengths of flexible tubing to provide fluid flow therethrough;
   (h) a collection reservoir for collecting cerebrospinal fluid, having an entry port and connected to the second length of flexible tubing through a drip chamber and having an outlet port from which cerebrospinal fluid can be removed.

21. A kit for externally draining cerebrospinal fluid from a patient, the kit comprising:
   (a) a ventricular drainage catheter for placement in the ventricles of a patient's brain for receiving cerebrospinal fluid;
   (b) a suture tab extending around the catheter for securing the catheter to the patient and preventing relative movement between the catheter and patient;
   (c) a three port stopcock connected to the catheter, which stopcock can be selectively opened and closed to fluid flow through the external ventricular drainage assembly;
   (d) a Y-tube connected to the three port stopcock and having a self-sealing injection port;
   (e) a one-way valve connected to the Y-tube;
   (f) a first length of flexible tubing connected to the one-way valve;
   (g) a coupling having a first member connected to the first length of flexible tubing and a second member connected to a second length of flexible tubing for interconnecting the first and second lengths of flexible tubing to provide fluid flow therethrough;
   (h) a collection reservoir for collecting cerebrospinal fluid, having an entry port and connected to the second length of flexible tubing through a drip chamber and having an outlet port from which cerebrospinal fluid can be removed.

22. A preassembled kit for externally draining cerebrospinal fluid from a patient, the kit comprising:
   (a) a ventricular drainage catheter for placement in the ventricles of a patient's brain for receiving cerebrospinal fluid;
   (b) a suture tab extending around the catheter for securing the catheter to the patient and preventing relative movement between the catheter and patient;
   (c) a three port stopcock connected to the catheter, which stopcock can be selectively opened and closed to fluid flow through the external ventricular drainage assembly;
   (d) a Y-tube connected to the three port stopcock and having a self-sealing injection port;
   (e) a one-way valve connected to the Y-tube;
   (f) a first length of flexible tubing connected to the one-way valve;
   (g) a coupling having a first member connected to the first length of flexible tubing and a second member connected to a second length of flexible tubing for interconnecting the first and second lengths of flexible tubing to provide fluid flow therethrough;
   (h) a collection reservoir for collecting cerebrospinal fluid, having an entry port and connected to the second length of flexible tubing through a drip chamber and having an outlet port from which cerebrospinal fluid can be removed.

* * * * *